US010485605B2

(12) United States Patent
Weinberg

(10) Patent No.: US 10,485,605 B2
(45) Date of Patent: Nov. 26, 2019

(54) SPATIALLY SELECTIVE INTERVENTIONAL NEUROPARTICLE WITH MAGNETOELECTRIC MATERIAL

(71) Applicant: Weinberg Medical Physics, Inc., North Bethesda, MD (US)

(72) Inventor: Irving N. Weinberg, North Bethesda, MD (US)

(73) Assignee: Weinberg Medical Physics, Inc., North Bethesda (*) Notice: Subject to any disclaimer, the term of this patent is extended or adjusted under 35 U.S.C. 154(b) by 52 days.

(21) Appl. No.: 15/614,061

(22) Filed: Jun. 5, 2017

(65) Prior Publication Data

US 2017/0265927 A1 Sep. 21, 2017

Related U.S. Application Data

(63) Continuation-in-part of application No. 15/466,133, filed on Mar. 22, 2017, now Pat. No. 10,231,774, (Continued)

(51) Int. Cl.

| | |
|---|---|
| ***A61B 18/12*** | (2006.01) |
| ***H01F 38/14*** | (2006.01) |
| ***A61N 1/372*** | (2006.01) |
| ***H02J 50/10*** | (2016.01) |
| ***A61N 1/36*** | (2006.01) |
| ***A61M 5/142*** | (2006.01) |
| ***A61B 18/18*** | (2006.01) |
| ***A61B 18/10*** | (2006.01) |
| ***A61N 1/378*** | (2006.01) |
| ***A61N 7/00*** | (2006.01) |

(Continued)

(52) U.S. Cl.

CPC ........ *A61B 18/1206* (2013.01); *A61B 5/0031* (2013.01); *A61B 5/04001* (2013.01); *A61B 5/04008* (2013.01); *A61B 5/40* (2013.01); *A61B 5/486* (2013.01); *A61B 18/10* (2013.01); *A61B 18/18* (2013.01); *A61F 7/00* (2013.01); *A61M 5/142* (2013.01); *A61N 1/36125* (2013.01); *A61N 1/3787* (2013.01); *A61N 1/37205* (2013.01); *A61N 7/00* (2013.01); *G06F 3/015* (2013.01); *H01F 38/14* (2013.01); *H02J 50/10* (2016.02); *H02J 50/80* (2016.02); *A61B 5/01* (2013.01); *A61B 5/055* (2013.01); *A61B 5/14546* (2013.01); *A61B 18/14* (2013.01); *A61B 2017/00221* (2013.01); *A61B 2018/00434* (2013.01); *A61B 2018/00613* (2013.01); *A61B 2034/2051* (2016.02); *A61B 2090/3954* (2016.02); *A61B 2560/0209* (2013.01); *A61B 2562/08* (2013.01); *A61N 2/006* (2013.01); *A61N 2007/0047* (2013.01)

(58) Field of Classification Search

CPC ................................................ A61B 18/10–18
USPC ............................................................. 607/1
See application file for complete search history.

(56) References Cited

U.S. PATENT DOCUMENTS

2009/0157151 A1* 6/2009 Cauller ................ A61B 5/6849 607/72

* cited by examiner

*Primary Examiner* — Amanda K Hulbert
*Assistant Examiner* — Philip C Edwards
(74) *Attorney, Agent, or Firm* — Barnes & Thornburg LLP

(57) ABSTRACT

An apparatus and method stimulate or sense neurons or groups of neurons in a subject, e.g., a human or animal brain, with positional dependence. This utility is provided in part by utilizing individually-addressable Radio-Frequency (Continued)

1
2
3

IDentification (RFID) coils so that locations of those coils in the brain would be monitored and known.

18 Claims, 1 Drawing Sheet

Related U.S. Application Data which is a continuation of application No. 14/221,777, filed on Mar. 21, 2014, now Pat. No. 9,622,809, which is a continuation-in-part of application No. 13/242,386, filed on Sep. 23, 2011, now abandoned.

(60) Provisional application No. 62/346,846, filed on Jun. 7, 2016, provisional application No. 61/894,097, filed on Oct. 22, 2013, provisional application No. 61/810,436, filed on Apr. 10, 2013, provisional application No. 61/804,094, filed on Mar. 21, 2013.

(51) Int. Cl.

| | |
|---|---|
| ***A61B 5/00*** | (2006.01) |
| ***A61B 5/04*** | (2006.01) |
| ***A61F 7/00*** | (2006.01) |
| ***G06F 3/01*** | (2006.01) |
| ***H02J 50/80*** | (2016.01) |
| ***A61N 2/00*** | (2006.01) |
| ***A61B 5/01*** | (2006.01) |
| ***A61B 5/055*** | (2006.01) |
| ***A61B 5/145*** | (2006.01) |
| ***A61B 18/14*** | (2006.01) |
| *A61B 17/00* | (2006.01) |
| *A61B 18/00* | (2006.01) |
| *A61B 34/20* | (2016.01) |
| *A61B 90/00* | (2016.01) |

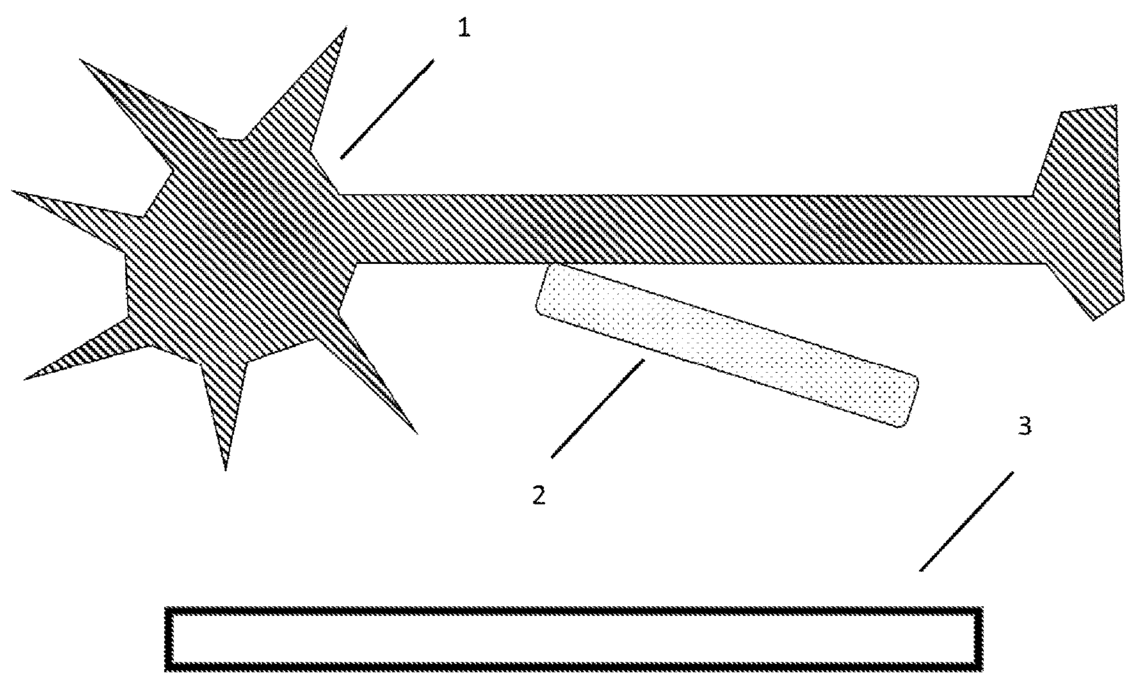
1
2
3

SPATIALLY SELECTIVE INTERVENTIONAL NEUROPARTICLE WITH MAGNETOELECTRIC MATERIAL

CROSS REFERENCE AND PRIORITY CLAIM

This patent application claims priority to U.S. Provisional Patent Application No. 62/346,846, entitled "Spatially Selective Interventional Neuroparticle with Magnetoelectric Material," filed Jun. 7, 2016, and to U.S. Non-provisional application Ser. No. 15/466,133, filed Mar. 22, 2017, entitled "Apparatus and Method for Spatially Selective Interventional Neuroparticles," which claims priority to the U.S. Non-provisional application Ser. No. 14/221,777, filed Mar. 21, 2014, entitled "Apparatus and Method for Spatially Selective Interventional Neuroparticles," which claims priority to U.S. Provisional Patent Application 61/804,094, filed Mar. 21, 2013, and entitled "Spatially Encoded Nano-stimulator," U.S. Provisional Patent Application 61/810,436, filed Apr. 10, 2013, and entitled "Neuroparticle," and U.S. Provisional Patent Application 61/894,097, filed Oct. 23, 2013, and entitled "Neuroparticle," and is Continuation in Part to U.S. Non-provisional application Ser. No. 13/242,386, filed Sep. 23, 2011, entitled "Flexible Methods of Fabricating Electromagnets and Resulting Electromagnet Elements," the disclosures of which being incorporated herein by reference in their entirety. As such, the present application is a technical implementation and extension of previously disclosed technology detailed in those applications and patent applications related by priority claims recited therein.

FIELD OF USE

Disclosed embodiments enable sensing and/or stimulation of neurons or collections of neurons in a human or animal brain for research or clinical or wellness or other purposes.

BACKGROUND

The ability to stimulate neurons or groups of neurons in the brain with implanted electrodes has been useful in conventional prostheses and brain-machine interfaces.

SUMMARY

Disclosed embodiments provide an apparatus and method for stimulating or sensing neurons or groups of neurons in the subject, e.g., a human or animal brain, with positional dependence.

Disclosed embodiments provide this utility by utilizing individually-addressable Radio-Frequency IDentification (RFID) coils so that locations of those coils in the brain can be monitored, known, and controlled.

BRIEF DESCRIPTION OF THE FIGURES

The detailed description particularly refers to the accompanying figures in which:

FIG. 1 illustrates an exemplary apparatus whereby one or more neurons may be electrically stimulated by one or more particles under the influence of at least one coil in accordance with the disclosed embodiments.

DETAILED DESCRIPTION

Disclosed embodiments provide an apparatus and method for stimulating neurons or groups of neurons in the subject of a human or animal brain with positional dependence. For the purpose of this disclosure, the term "positional dependence" is defined as providing a means of stimulating neurons that are located in one position and not in another. Disclosed embodiments provide this utility by utilizing individually-addressable Radio-Frequency IDentification (RFID) coils so that locations of those coils in the brain would be monitored and known.

Work has been published on the use of RFID tags by Alham Moradi et al, in the article "Backscattering Neural Tags for Wireless Brain-Machine Interface Systems", in the journal IEEE Transactions on Antennas and Propagation, vol. 63, number 2, 2015 (incorporated by reference in its entirety). The spatial resolution of such an innovation would be defined by the size of an RFID antenna, which would typically be on the order of 1 mm (as in Moradi et al.) because the efficiency of coupling to the RFID would depend on the size of the antenna. As a result, a smaller antenna would not be effective in such a conventional set up.

In accordance with disclosed embodiments, RFID devices with magneto-electric sections, may be deployed into the brain of human or animal subjects. Such RFID devices may be configured to act as receivers of data and/or instructions via radio frequency signals and/or transmitters of data and/or instructions via radio frequency signals.

For the purpose of this disclosure, the term "device" is used to include implanted RFID devices. For the purpose of this disclosure, the term "implanted" includes devices introduced into the brain or nervous system whether with a needle or in some other manner, for example, introduced via the nose or vein or spinal canal.

Disclosed embodiments use the magneto-electric material in the RFID devices to reduce the size of the implanted RFID devices considerably. As a result of reducing the size of the implanted RFID devices, disclosed embodiments thereby improve the spatial resolution of such devices.

In the paper by R Petrov et al entitled "Miniature antenna based on magnetoelectric composites," published in the Journal Electronic Letters 44(8):506-707 in January 2008 (incorporated by reference), it was shown that the size of an antenna could be reduced by a factor of seven.

Thus, reducing the size of the RFID antenna would enable the RFID to exhibit higher spatial resolution than would otherwise be possible conventionally. Therefore, for example, the RFID device(s) may have dimensions, and or features that are less than 100 microns, less than 10 microns, or even less than 1 micron.

For the purpose of this proposal, the terms "magnetoelectric material" or "magneto-electric material" or "magneto-electric composite" or "magneto-electric composite" is defined as a substance or combination of substances which changes its electric properties in the presence of a magnetic field, and/or which changes its magnetic properties in the presence of an electric field.

In accordance with at least one embodiment, the magneto-electric composite may be a single material exhibiting both magnetic and electric properties, for example, $Cr_2O_3$ and $BiFeO_3$. Alternatively, the magneto-electric material may be a composite of piezoelectric and magnetostrictive materials, such as $BaTiO_3$—$CoFe_2O_4$.

FIG. 1 illustrates an exemplary apparatus whereby at least one neuron 1 is electrically stimulated by at least one particle 2 under the influence of at least one coil 3.

In accordance with at least one embodiment, coil 3 may be located outside the body of the human or animal subject, and may be used to sense and/or stimulate the at least one particle 2.

It should be understood that the particle 2 may consist of the RFID device only or also include other components including but not limited to other devices for sensing and/or stimulating neurons in the human body. For example, the at least one particle 2 may include the RFID device as well as nano- and micro-engineered electromagnetic devices to stimulate and/or sense the state of portions of the nervous system in vivo. For example, as discussed in FIG. 1 of U.S. Ser. No. 14/221,777, incorporated by reference in its entirety, such electromagnetic devices may include but are not limited to devices that employ or are sensitive to electrical and/or magnetic energy, for example, spintronic devices or CMOS-fabricated circuits. Thus, such electromagnetic devices may include, for example, a transducer that is near to or at least partially surrounds a core of magnetizable material, configured such that electromagnetic device is capable of collecting energy transmitted by a transmission device (see 100 of FIG. 2 in U.S. Ser. No. 14/221,777) that is external to a subject's body.

As a result, it should be appreciated that the shape of the particle 2 may be dictated at least in part by what components are included in the particle 2. Accordingly, any illustration of the particle is merely representative and not limiting to the scope of the disclosed embodiments.

For example, the presently discussed power source and at least one radio frequency antenna coupled together and located external to a living body for transmitting energy to the components within the subject's body may include components illustrated in FIG. 2. Such electromagnetic devices may include a transducer, which converts ambient electromagnetic energy into electrical energy that can be stored or modified within the electromagnetic device. In implementation such a transducer may include coil elements wound or otherwise placed around a magnetizable core, although other types of magnetic sensors (e.g., magnetostrictive, ferroelectric, magnetocapacitative, piezoelectric cantilever devices) could be used. It should be understood that the use of magnetic materials to move portions of mechanical generators (e.g., tribological generators) may also be included in the category of transducers.

Likewise, the transducer may be connected electrically through resistive and other circuit elements (for example, diodes) to an energy storage device, e.g., a capacitor or the transducer may contain its own functional capacitance enabling it to store energy. Such stored energy may be used to power or activate one or more circuits including antennae and/or contacts for stimulation of nearby tissue of a subject. Optionally, the stored energy may be used to power the RFID device in the particle 2 to enable communication with and/or control of the particle by the external antenna power source combination.

Thus, in accordance with at least one embodiment, the magneto-electric composite of the RFID device of the particle 2 may act as a receiver to collect radiation from one or more external transmitters of RF energy, and create a local voltage depending on the frequency or combination of frequencies emitted by the external transmitter.

In accordance with at least one embodiment, the RFID device(s) may contain a piezoelectric component that may be activated by a current through the device in order to deliver an electrical voltage to the surrounding neuron or neurons.

Transmission of energy to the particle 2 to generate these voltages and/or currents via a RFID device included therein may be performed in a manner consistent with or similar to the operations discussed in FIGS. 1-4 of U.S. Ser. No. 14/221,777, incorporated herein by reference. More specifically, those figures and their associated textual disclosure and description provide examples of how an electromagnetic device that may be provided to be resident in a nervous system may receive energy transfer from an energy transmitting device located outside of a subject's body into the device.

Thus, it should be understood that components of the particle, for example, electromagnetic devices for stimulating or sensing a milieu for, e.g., one or more neurons, may be powered using energy harvested by a transducer in the device or from energy transmitted to and received by the RFID device in the particle. In either implementation, energy received at the particle may, for example, result in application of pulses to nearby tissues can be of many types, using components of the electromagnetic device, e.g., through a resistive element and/or diode or other electronic component or power conditioning circuit into a capacitor or other energy storage device. Accordingly, power from the storage device may then be applied to an oscillator circuit. Details of this configuration and the associated functionality may be found in U.S. Ser. No. 14/221,777. One of ordinary skill in the art should recognize that the presently disclosed RFID device included in the particle 2 illustrated in FIG. 1 may include components similar to or included in the electromagnetic device disclosed in U.S. Ser. No. 14/221,777. The extension of that innovation disclosed herein including the ability to reduce the size of RFID devices, and thereby, particle size, as a result of using the magneto-electric material in the RFID devices in a novel way.

The magneto-electric material may be fabricated in various ways, including, for example, as disclosed in U.S. Non-Provisional application Ser. No. 13/242,386,entitled "Flexible Methods of Fabricating Electromagnets and Resulting Electromagnet Elements," filed Sep. 23, 2011 (incorporated herein by reference).

To the extent that the disclosed embodiments provide a particle(s) for sensing the milieu in which the particle, it should be understood that one or more sensors may be included in the particle for sensing one or more characteristics of the milieu, e.g., the magnetic field, voltage, current, chemical substances, receptors, temperature, and/or pressure, etc. Because of the decrease in size of the RFID device required for communication with or control of the components of the particle 2, the remaining components can be increased in size, complexity or quantity to increase the utility or functionality provided by the particle(s).

In accordance with at least one embodiment, the RFID device(s) may be configured to transmit or report data indicating its location to an external receiver, that is, a RF receiver that is external to the body of the human or animal subject. For example, as explained in U.S. Ser. No. 14/221,777, incorporated herein by reference, the disclosed embodiments may use nano- and micro-engineered electromagnetic devices to stimulate and/or sense the state of portions of the nervous system in vivo. Thus, in accordance with the embodiments disclosed herein, a particle introduced into the body of a living subject may include an RFID device to enable communication with and control of a nano- or micro-engineered electromagnetic device also included in the particle. Accordingly, it should be appreciated that the components of the particle, e.g. the RFID device including the RFID antenna and nano- or micro-engineered electromagnetic devices may be coupled together for control and communication therebetween.

Various operations may be performed and/or types of information may be detected, monitored or sensed by the particles provided in accordance with the disclosed embodiments. For example, because a transducer in an electromagnetic device may be made sensitive to a magnetic field strength and/or orientation by saturation of core structure (as discussed in patent application Ser. No. 14/221,777) or by operation and coupling and communication with the presently disclosed RFID device included in particle 2, the magnetic environment in which the particle is positioned can be sensed by the particle and/or affect internal operation and subsequent activities of the components of the particle 2.

Thus, it should be understood that the particles 2 may be transported through a subject's body and/or nervous system as a result of the application of magnetic gradients that may act on the magnetizable materials included in the components of the particles. Such transportation is taught by I N Weinberg, M G Urdaneta, P Y Stepanov, D Beylin, A Nacev, A Sarwar, B Shapiro, O C Rodriguez, C Albanese, R Probst, and S T Fricke, in the article entitled "Non-invasive Image-Guided Brain Access with Gradient Propulsion of Magnetic Nanoparticles", published in the Proceedings of the 2012 IEEE Medical Imaging Conference (incorporated herein by reference in its entirety). It should be understood that magnetic pulses to affect such imaging, or to affect magnetic resonance imaging of the body, may be applied at different times from the magnetic field pulses for communicating with, powering and/or controlling the particle(s) 2 in order to implement image guidance.

Further, it should be understood that, depending on the structure and function of the electromagnetic device included in a particle 2, the particle can be used to determine the electrical and/or chemical milieu where it is located, through amplification of signals from the milieu obtained through the RFID device or additional antennae specific to the electromagnetic device included in particle 2.

Further, core material in such an electromagnetic device may be used as a means of spatially-localizing the particle in the subject's body, and the location and status in the body could be determined through comparison of signals sensed by external antennas and/or components of antennas or other sensing devices located at different positions and/or orientations with respect to the subject's body.

Finally, as explained in detail in U.S. Ser. No. 14/221,777, a plurality of particles 2 could be introduced into a subject's body and the concentration of numbers of particles could be imaged through analysis of magnetization properties or by emission of energy from the devices. Likewise, it should be understood that a plurality of particles 2 could act within one or more regions of space, and at one or more times, to cause stimulation of nerve tissue.

In accordance with at least one embodiment, the particle 2 including the RFID devices may be coated with materials that would enhance its penetration or retention within or near a neuron or neurons. For example, the particle 2 may be coated with a bio-compatible material having properties enabling it to effectively target or reside in certain cell types or in certain portions of cells, e.g., lipophilic materials specific to a cell membrane of a neuron.

In accordance with at least one embodiment, the location of the RFID device(s) may be detected with a magnetic resonance or magnetic particle or electrical imaging device.

In accordance with at least one embodiment, the RFID devices may respond selectively to a set of emanations from an external RF source. An example of such frequency selectivity is taught by MD Imdul Reza Shishir et al, published in Structural Control Health Monitoring electronically under DOI: 10.1002/stc.2028, and entitled "Frequency-selective surface-based chipless passive RFID sensor for detecting damage location" (incorporated by reference in its entirety). As in the publication by Reza Shishir, the RFID device could be composed of a frequency-selective meta-material antenna, whose electromagnetic characteristics are associated with electrical impedance and mechanical shape. For the purpose of this disclosure, the frequency-selective meta-material or composite material may also have magnetic properties that add to frequency selectivity when the material is subjected to a magnetic and/or electromagnetic field.

As explained above, disclosed embodiments further enable sensing and/or stimulation of neurons or collections of neurons in a human or animal brain for research or clinical purposes. More specifically, disclosed embodiments may be utilized to stimulate or otherwise affect portions of the nervous system of a subject's body without affecting other portions of the nervous system. For example, the presently disclosed embodiments may be used to apply the principle of selecting zones magnetically to specify spatial locations in which very small circuits can be activated, and which once activated may stimulate, affect, and/or sense nearby tissues.

Although the term "stimulate" is used as an illustration of the mechanism for increasing the firing rate of neurons, it should be understood that the disclosed embodiments may also be used to decrease the firing rate of neurons (i.e., inhibit firing) by repeatedly stimulating neurons (e.g., by depleting stores of neurotransmitters) or by shorting electrical circuitry in neurons, or by heating nearby tissues, or electroporating nearby tissues, or through other neurophysiological means.

It should be understood that the effect on nearby tissues may be destructive, as would be desirable if the tissues were malignant or causing epilepsy or tremors to occur. In such a situation, the tissues affected might be other than neuronal tissues. The destruction could be immediate, or could result in long-term damage as might affect the ability of the cells to reproduce, or could potentiate other means of affecting tissues (e.g., by sensitizing tissue to subsequent radiation therapy).

In accordance with at least one disclosed embodiment an apparatus and method are provided for spatially-selective administration of actions by at least one device in the body using a transducer that is sensitive to a spatially-variant energy field imposed on the at least one device by a source external to a subject's body; and at least one component in the at least one device, wherein interaction of the transducer with the imposed spatially-variant energy field causes or enables at least one component in the at least one device to affect nearby tissues in the body.

It should be understood that operations explained herein, e.g., control of and communication with the RFID devices(s) external to the subject may be implemented in conjunction with, or under the control of, one or more general purpose computers running software algorithms to provide the presently disclosed functionality and turning those computers into specific purpose computers.

Moreover, those skilled in the art will recognize, upon consideration of the above teachings, that the above exemplary embodiments may perform the above-specified operations (and those referred in the claims) under the control of at least one controller that may utilize or be based upon use of one or more programmed processors programmed with a suitable computer program. However, the disclosed embodiments could utilize one or more controllers implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Furthermore, it should be understood that control and cooperation of components of an instrument for applying magnetic fields described herein to manipulate the one or more particles including the RFID device(s) may be provided using software instructions that may be stored in a tangible, non-transitory storage device such as a non-transitory computer readable storage device storing instructions which, when executed on one or more programmed processors, carry out the above-described method operations and resulting functionality. In this case, the term non-transitory is intended to preclude transmitted signals and propagating waves, but not storage devices that are erasable or dependent upon power sources to retain information.

Accordingly, such an instrument may include one or more controllable electromagnetic field sources and a controller that enables control of resulting magnetic fields, e.g., spatially variant magnetic fields, as described herein. In one such implementation, one or more gradient coils may be utilized under the control of a controller to enables control of the gradient to produce one or magnetic fields using at least one coil driver, wherein one or more coils are provided for transmitting RF energy into a tissue sample of a body part as part of diagnostic, prognostic, and/or treatment.

Those skilled in the art will appreciate, upon consideration of the above teachings, that the program operations and processes and associated data used to implement certain of the embodiments described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies without departing from certain embodiments of the present invention. Such alternative storage devices should be considered equivalents.

While certain illustrative embodiments have been described, it is evident that many alternatives, modifications, permutations and variations will become apparent to those skilled in the art in light of the foregoing description. While illustrated embodiments have been outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

As a result, it will be apparent for those skilled in the art that the illustrative embodiments described are only examples and that various modifications can be made within the scope of the invention as defined in the appended claims.

The invention claimed is:

1. An apparatus comprising:

a power source and at least one radio frequency antenna, coupled together and located external to a living body; and at least one radio particle including a frequency identification device (RFID) introduced internal to the living body, wherein the at least one particle's RFID includes magnetoelectric material, wherein the at least one particle's RFID is situated in or near one or more neurons within the living body, and wherein the at least one internally-located particle includes components controlled using the externally-located radio-frequency antenna to selectively stimulate or sense at least one characteristic of the one or more neurons in response to a selective emanation from the externally-located radio frequency antenna.

2. The apparatus of claim 1, wherein the at least one RFID device has dimensions less than 100 microns.

3. The apparatus of claim 1, wherein the at least one RFID device has dimensions less than 10 microns.

4. The apparatus of claim 1, wherein the at least one RFID device has dimensions less than 1 micron.

5. The apparatus of claim 1, wherein the at least one particle includes at least one electromagnetic device for stimulating or sensing one or more neurons or groups of neurons in the living body with positional dependence.

6. The apparatus of claim 1, wherein the at least one particle is one of a plurality of particles each including an RFID device, wherein each RFID device includes individually-addressable coils, which enable monitoring locations of those coils in the living body.

7. The apparatus of claim 1, wherein the at least one internally-located particle includes components controlled using the externally radio-frequency antenna to selectively stimulate the one or more neurons in response to a selective emanation from the externally-located radio frequency antenna with positional dependence.

8. The apparatus of claim 1, wherein the RFID device is configured to act as a receiver of data and/or instructions via radio frequency signals emitted by the at least one externally located radio frequency transmitter.

9. The apparatus of claim 1, wherein the RFID device includes an RFID material made of magneto-electric composite material that exhibits both magnetic and electric properties.

10. A method comprising:

positioning a power source and at least one radio frequency antenna, coupled together external to a living body;

introducing at least one radio particle including a frequency identification device (RFID) internal to the living body, wherein the at least one particle's RFID includes magnetoelectric material;

positioning the at least one particle's RFID is situated in or near one or more neurons within the living body; and controlling the at least one internally-located particle using the externally radio-frequency antenna to selectively stimulate or sense at least one characteristic of the one or more neurons in response to a selective emanation from the externally-located radio frequency antenna.

11. The method of claim 10, wherein the at least one RFID device has dimensions less than 100 microns.

12. The method of claim 10, wherein the at least one RFID device has dimensions less than 10 microns.

13. The method of claim 10, wherein the at least one RFID device has dimensions less than 1 micron.

14. The method of claim 10, wherein the at least one particle includes at least one electromagnetic device for stimulating or sensing one or more neurons or groups of neurons in the living body with positional dependence.

15. The method of claim 10, wherein the at least one particle is one of a plurality of particles each including an RFID device, wherein each RFID device includes individually-addressable coils, which enable monitoring locations of those coils in the living body.

16. The method of claim 10, wherein the at least one internally-located particle includes components controlled using the externally radio-frequency antenna to selectively stimulate the one or more neurons in response to a selective emanation from the externally-located radio frequency antenna with positional dependence.

17. The method of claim 10, wherein the RFID device is configured to act as a receiver of data and/or instructions via radio frequency signals emitted by the at least one externally located radio frequency transmitter.

18. The method of claim 10, wherein the RFID device includes an RFID material made of magneto-electric composite material that exhibits both magnetic and electric properties.

* * * * *